(12) United States Patent
Roa et al.

(10) Patent No.: US 8,440,442 B2
(45) Date of Patent: May 14, 2013

(54) METHOD OF ASSAYING 5-FU

(75) Inventors: Benjamin Roa, Salt Lake City, UT (US); Carrie Colvin, Salt Lake City, UT (US); Michael Overfield, Salt Lake City, UT (US); Howard McLeod, Chapel Hill, NC (US); Salvatore Salamone, Bethlehem, PA (US)

(73) Assignee: Myriad Genetics, Inc, Salt Lake City, UT (US)

( * ) Notice: Subject to any disclaimer, the term of this patent is extended or adjusted under 35 U.S.C. 154(b) by 190 days.

(21) Appl. No.: 12/839,336

(22) Filed: Jul. 19, 2010

(65) Prior Publication Data

US 2011/0034488 A1 Feb. 10, 2011

Related U.S. Application Data (60) Provisional application No. 61/226,589, filed on Jul. 17, 2009, provisional application No. 61/324,241, filed on Apr. 14, 2010.

(51) Int. Cl.
*C12N 9/00* (2006.01)
*C12Q 1/00* (2006.01)

(52) U.S. Cl.
USPC .............................. 435/183; 435/4

(58) Field of Classification Search ...................... None
See application file for complete search history.

(56) References Cited

U.S. PATENT DOCUMENTS

| 7,205,116 B2 | 4/2007 | Salamone et al. |
| 2007/0134251 A1 | 6/2007 | Ashkenazi et al. |
| 2007/0225245 A1 | 9/2007 | Buchsbaum et al. |

OTHER PUBLICATIONS

Beumer et al., "5-Fluorouracil Measurement by Liquid Chromatography/Tandem Mass Spectrometry and Stability in Human Blood and Plasma", (pp. 417-419) From: 'Highlights from: 5-Fluorouracil Drug Management Pharmacokinetics and Pharmacogenomics Workshop', Orlando, FL; Jan. 2007; Clinical Colorectal Cancer, Mar. 2007; vol. 6, Issue 6, pp. 407-422.*
Tatsumi et al., "Inhibitory Effects of Pyrimidine, Barbituric Acid and Pyridine Derivatives on 5-Fluorouracil Degradation in Rat Liver Extracts", Jpn. J. Cancer Res. (Gann), 1987, 78:748-755.*

* cited by examiner

*Primary Examiner* — Suzanne M Noakes
(74) *Attorney, Agent, or Firm* — Benjamin G. Jackson; Matthew S. Gordon; Myriad Genetics IP Department (57) ABSTRACT

The present invention provides methods, compositions, devices and kits for assaying 5-FU.

15 Claims, 9 Drawing Sheets

METHOD OF ASSAYING 5-FU

RELATED US APPLICATIONS

This application claims the benefit of U.S. Provisional Application No. 61/324,241 filed on Apr. 14, 2010, and U.S. Provisional Application No. 61/226,589 filed on Jul. 17, 2009, the entire content of both of which is incorporated herein by reference.

FIELD OF THE INVENTION

The invention generally relates to diagnostic testing, and particularly to a composition and diagnostic method for assaying 5-fluorouracil in patient samples.

BACKGROUND OF THE INVENTION 5-fluorouracil (5-FU) is one of the most important chemotherapeutics in cancer treatment. It is commonly used in various chemotherapy regimens for colorectal, stomach, breast and pancreatic cancers. For example, 5-FU alone or in combination regimens such as FOLFOX and FOFIRI is the standard first line therapy in metastatic colorectal cancer. However, 5-FU is frequently associated with severe adverse effects including myelosuppression, mucositis, dermatitis, diarrhea, cardiac toxicity and even death. These adverse effects are caused at least in part by the current approach to dose determination for individual patients. The current standard of care for dosing—Body Surface Area (BSA)—only takes into account a patient's height and weight. BSA does not account for many of the factors that impact 5-FU metabolism and efficacy such as genotype, age, gender, disease state, drug-drug interactions, organ function, and comorbidities. It is therefore not so surprising that blood concentrations of 5-FU in different patients can vary by more than ten fold despite BSA-based equal dose administration.

Recent academic studies have shown that individual 5-FU dose adjustment based on pharmacokinetic monitoring of plasma 5-FU concentrations can result in significantly improved objective response rate to 5-FU. See e.g., Gemelin et al. *J. Clin. Oncol.*, 26(13):2099-2105 (2008); Climente-Marti et al., *J. Pharmaceut. Sci.*, 92(6):1155-1165 (2003); Milano et al., *Int. J. Cancer*, 41:537-541 (1988). These studies suggest that clinical testing of 5-FU blood concentrations in individual patients undergoing 5-FU therapy is clearly desirable for the purpose of 5-FU dose adjustment, optimization of therapeutic effect, and reduction of severe adverse reactions.

SUMMARY OF THE INVENTION

The present invention generally provides a method of assaying 5-fluorouracil (5-FU) in a patient sample.

In a first aspect, a method is provided for assaying 5-FU in a sample from a patient administered 5-FU and optionally other therapeutics. In the method, a sample is obtained from a patient administered 5-FU. The sample is then mixed with an inactivator of dihydropyrimide dehydrogenase (DPD), and the amount of 5-FU is measured in the sample preferably in admixture with the DPD inactivator.

In another aspect, the present invention provides a method of treating a patient with 5-FU, comprising the steps of: administering to the patient a first dose of 5-fluorouracil; determining the amount of 5-FU in a sample obtained from the patient administered with 5-FU, wherein said sample is admixed in vitro with an inactivator of DPD, and wherein the amount of 5-FU in said sample is measured preferably in the presence of the inactivator; and administering to the patient a second dose of 5-FU. The amount of 5-FU administered in the second dose can be determined based on the measured 5-FU level in the patient sample in reference to a predetermined optimal or target 5-FU AUC.

The present invention also provides methods of processing a blood sample from a patient undergoing a therapy with 5-FU and optionally other drugs, for a 5-FU assay. In one embodiment, the method includes the following steps: obtaining a blood sample containing 5-FU from a patient administered 5-FU; isolating plasma from the blood sample; admixing the separated plasma with an inactivator of DPD to form a mixture; and sending the mixture to a laboratory for diagnostic testing for the level of 5-FU in the mixture.

In another embodiment, the method comprises the steps of: obtaining a blood sample containing 5-fluorouracil from a patient administered 5-FU; admixing the blood sample with a DPD inactivator to form a mixture; and isolating plasma containing 5-fluorouracil and the inactivator from the mixture. The thus obtained plasma can be sent to a laboratory for assaying 5-FU.

In yet another embodiment, the method of processing a blood sample from a patient administered 5-FU entails the following steps: obtaining a blood sample containing 5-FU from the patient; admixing the blood sample with a DPD inactivator to form a mixture; and sending the mixture to a laboratory for assaying 5-FU.

In yet another aspect of the present invention, a composition is provided comprising a sample isolated from a patient administered 5-FU, in admixture with an inactivator of dihydropyrimide dehydrogenase, wherein said sample is blood or plasma or serum, and the inactivator is at a concentration of at least 850 ng/ml in the composition.

In another aspect, the present invention provides a kit having in a container: (a) a sample (blood, plasma or serum) isolated from a patient administered 5-FU, in admixture with an inactivator of DPD at a concentration of at least 850 ng/ml; and (b) means for cooling said sample to a temperature below 10° C.

In the various aspects of the present invention, preferably the sample is not frozen within 5 to 10 hours after separation from said patient. Examples of the inactivator include, e.g., pyrimidine or pyridine derivatives, particularly uracil analogs such as eniluracil and gimeracil. 5-FU can be assayed in a sample by any known techniques, e.g., HPLC, Mass-Spec, or immunoassays using antibodies against 5-FU.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

I. Sample Preparation, 5-FU Assay, Compositions and Kits

In accordance with a first aspect of the present invention, a method is provided for processing patient samples containing 5-FU (e.g., from patients treated with 5-FU or a prodrug of 5-FU) for use in a 5-FU assay. The method results in increased stability of 5-fluorouracil in the samples and significantly improved accuracy of 5-FU measurements. Thus, in another aspect, the present invention also provides a method of assaying 5-FU using a patient sample processed according to the processing method. Generally, the processing method comprises the steps of obtaining a sample containing 5-FU (e.g., from a patient administered 5-FU or a prodrug of 5-FU); admixing the sample with an inactivator of dihydropyrimide dehydrogenase to form a mixture; and sending mixture to a laboratory for assaying 5-FU in the mixture.

It is noted that while the embodiments of the present invention are described in details in the context of patient samples obtained from a patient treated with 5-FU, the present invention would also encompass patient samples obtained from a patient treated with a prodrug of 5-FU. Such a prodrug (e.g., tegafur, doxifluridine, and capecitabine) is metabolically activated inside the patient's body and converted into 5-FU.

The 5-FU-containing patient sample used in the present invention can be from any patient administered 5-FU in whom 5-FU level is to be measured. It can also be from patients administered one or more 5-FU prodrugs such as tegafur, doxifluridine, and capecitabine. For example, 5-FU is commonly used in chemotherapy for cancer patients including patients with breast cancer, lung cancer, colorectal cancer, pancreatic cancer or head and neck cancer. 5-FU is also used in ophthalmic surgery in glaucoma patients as an anti-scarring agent at the trabeculectomy site. In addition, 5-FU is used topically as a cream for treating Bowen's disease, solar keratoses, and basal cell carcinomas of the skin. The methods of the present invention are particularly advantageous for assaying 5-FU in cancer patient samples. In this context, the patient can be a cancer patient undergoing a treatment regimen comprising 5-FU. For example, 5-FU is typically administered along with folic acid or leucovorin. In metastatic colon cancer, 5-FU is often used in combination regimens such as FOLFOX (5-FU plus oxaliplatin and leucovorin) and FOLFIRI (5-FU plus irinotecan and leucovorin). Newer drugs such as bevacizumab, panitumumab and cetuximab may also be added to the regimens. The present invention is applicable in all such therapies and treatment regimens for assaying 5-FU in samples obtained from patients being treated with such regimens, and to optimizing the amount 5-FU administered to a particular patient.

Patient samples suitable for use in the present invention can be from any part of the body of a patient. For example, suitable samples can be tissue or bodily samples, such as tumor tissues, blood, plasma, serum, urine, etc.

In cancer therapies, 5-fluorouracil is typically administered by intravenous bolus injection or intravenous infusion. The administration can be repeated daily, weekly, every four weeks, depending on the choice of treatment regimen. Bolus injection can be given over 1 to 10 minutes or over 20 to 60 minutes, and for example, can be repeated for 5 consecutive days, every four week for 6 cycles. In continuous IV infusion, 5-FU can be administered over several hours, e.g., in 8 hours on a weekly basis. Blood samples can be drawn from a patient at any time before, after or during the administration of 5-FU. Often times, measuring blood 5-FU level at a steady state is desirable, in which case blood samples are drawn after a steady state is reached. For example in an eight-hour continuous infusion, a steady state can be reached two hours after the initiation of the infusion.

Typically, blood samples can be collected in any conventional ways of drawing peripheral venous blood. For example, a blood sample can be collected into a tube or vial typically used in clinics. The amount of blood collected depends on the amount required for a particular 5-FU assay. For example, 1 milliliter to 2 milliliters to 5 milliliters to 10 milliliters can be sufficient for most types of 5-FU assays. Optionally, EDTA or heparin may be mixed with the blood sample to prevent clotting. The mixing can be achieved by e.g., using a heparinized tube or an EDTA tube.

In accordance with the present invention, the obtained patient sample containing 5-FU is then admixed with an inactivator of dihydropyrimidine dehydrogenase (DPD) in vitro to inhibit the DPD activity and prevent 5-FU degradation. The patient sample can be chilled at a temperature of about 0° C., e.g., for at about 5 minutes or longer before a DPD inactivator is added to the patient sample and mixed together. But preferably, the patient sample is admixed with a DPD inactivator immediately after its separation from the patient's body. The resulting mixture (patient sample in admixture with a DPD inactivator) can then be sent to a laboratory for assaying the amount or level or concentration of 5-FU in the sample.

In one embodiment, the method of processing a patient sample for a 5-FU assay comprises obtaining a blood sample containing 5-fluorouracil from a patient administered 5-FU or a 5-FU prodrug, admixing the blood sample with a DPD inactivator to form a mixture, and optionally sending the mixture to a laboratory for assaying the amount of 5-FU in the patient sample.

In another embodiment, the method of processing a patient sample for a 5-FU assay comprises obtaining a blood sample containing 5-FU from a patient treated with 5-FU or a 5-FU prodrug, admixing the blood sample with an inactivator of dihydropyrimide dehydrogenase to form a mixture, isolating plasma containing 5-FU and the inactivator from the mixture; and optionally sending the plasma to a laboratory for assaying 5-FU level. In preferred embodiments, the admixing step takes place immediately after the blood sample is drawn from a patient. That is, after the blood sample is separated from the patient's body, a DPD inactivator should be added to and admixed with the collected blood sample as soon as practical. Also preferably the step of isolating plasma from the blood sample admixed with a DPD inactivator is performed within 4 or 5 hours, more preferably within 1 hour, from the time the blood is drawn.

In another embodiment, the method of processing a patient sample for a 5-FU assay comprises obtaining a blood sample containing 5-FU from a patient treated with 5-FU or a 5-FU prodrug, isolating plasma from the blood sample, admixing the separated plasma with a DPD inactivator to form a mixture, and sending the mixture to a laboratory for assaying 5-FU level.

Figure 1:
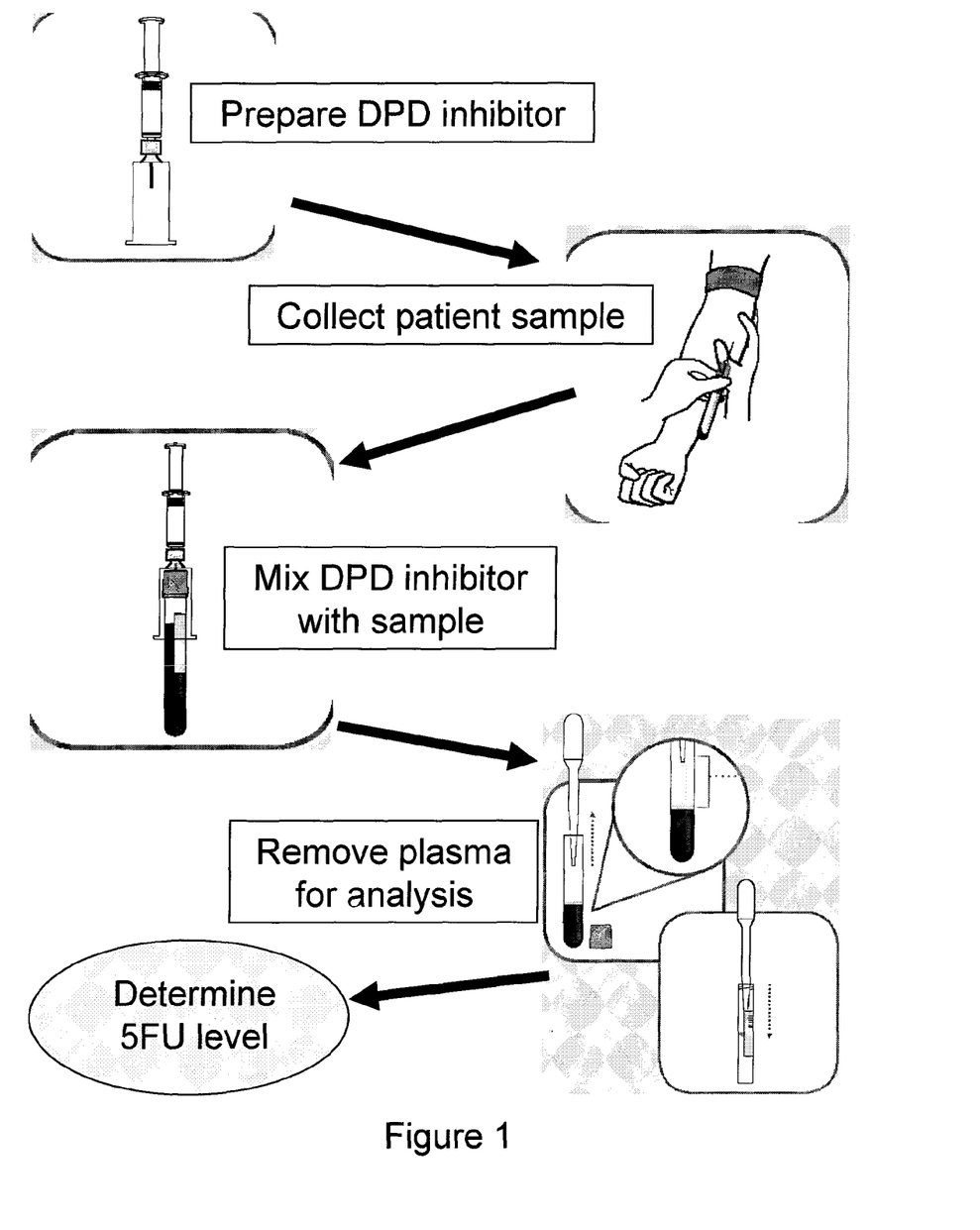
FIG. 1 is a diagram demonstrating an embodiment the sample processing method implemented in a clinic setting.

FIG. 1 demonstrates how the sample processing method can be implemented in a clinic. A DPD inactivator syringe (containing DPD inactivator solution) and a transfer device can be prepared as illustrated in FIG. 1. Specifically, the cap of a DPD inactivator syringe (see also FIG. 6) is unscrewed, the syringe is connected to the BD Transfer Device (see also FIG. 7), and the combined unit is set aside until the blood sample has been collected. Patient blood can be drawn as shown in FIG. 1. Specifically, blood can be drawn into a 6-mL K2-EDTA Vacutainer® tube while the patient is still being continuously infused with 5-FU at the prescribed infusion rate. Blood is drawn from a peripheral vein, not from the infusion port, at least 2 hours after the start of 5-FU continuous infusion. Blood is drawn until the tube is, e.g., at least ¾ full, and preferably the exact 5-FU dose administered in mg/m² and the total infusion duration are recorded. A DPD inactivator solution is then immediately dispensed into the blood sample tube as shown in FIG. 1. Specifically, the combined syringe-transfer device unit is connected over the K2-EDTA tube and firmly inserted through the tube stopper, after which the syringe plunger is completely depressed. The sample is then gently mixed by inverting the tube at least 3 times. Plasma is separated by centrifugation at 1,500 g-2,000 g for 10 minutes. Finally, no more than half of the plasma is removed with a disposable pipette and transferred into a 3-mL Cryovial® tube as illustrated in FIG. 1. Specifically, the bulb of the disposable pipette is squeezed before inserting the tip into the plasma. Then, the pipette tip is inserted just beneath the top of the clear plasma layer and the bulb is slowly released. The pipette is tracked down the tube as the plasma is drawn. No more than half of the clear plasma layer is drawn into the pipette and repeated aspiration is avoided so as to prevent disturbing the buffy coat/cellular layer between the plasma and red blood cells. The plasma is transferred from the pipette to the 3-mL Cryovial tube for storage and 5-FU level analysis.

Inactivators of DPD are generally known in the art. DPD (dihydropyrimidine dehydrogenase, EC 1.3.1.2) is an enzyme that catalyzes the reversible reduction of pyrimidines to 5,6-dihydropyrimidines. As used herein, the term "inactivator of DPD" or paraphrases thereof shall mean any organic or inorganic molecule that inhibits the enzymatic activity of DPD, i.e., its ability to catalyze the reduction of pyrimidine or 5-FU. The term "inactivator of DPD" does not encompass 5-FU. Examples of the inactivator include, e.g., pyrimidine derivatives, pyridine derivatives, and babituric acid derivatives. In some embodiments, the DPD inactivator is a DPD inhibitor, preferably an irreversible DPD inhibitor. In some embodiments, the DPD inactivator is a uracil derivative, i.e., a uracil compound substituted in the 5-position by a moiety chosen from halogen atom, a $C_{2-4}$ alkenyl group, a $C_{2-4}$ haloalkenyl, a $C_{2-6}$ alkynyl group, a $C_{2-6}$ haloalkynyl group, a cyano group, a $C_{1-4}$ alkyl group and a $C_{1-4}$ haloalkyl group. In specific embodiments, the DPD inactivator is a uracil derivative selected from the group consisting of eniluracil, 5-propynyluracil, 5-cyanouracil, 5-bromoethynyluracil, 5-(1-chlorovinyl)uracil, 5-iodouracil, 5-bromovinyluracil, (E)-5-(2-bromovinyl)uracil, 5-hex-1-ynyluracil, 5-vinyluracil, 5-trifluorouracil, 5-bromouracil and 5-(2-bromo-1-chlorovinyl)uracil. In some embodiments, the DPD inactivator used is chosen from derivatives of barbituric acid, derivatives of 2,4-dihydroxypyridine and derivatives of 2,6-dihydroxypyridine.

In some embodiments, the DPD inactivator is a pyridine derivative. In specific embodiments, the DPD inactivator used is gimeracil (5-chloro-2,4-dihydroxypyridine) or 3-cyano-2,6-dihydroxypyridine.

While the phrase "a DPD inactivator" is used herein, it is really meant "one or more DPD inactivators" as will be clear to a skilled artisan apprised of this disclosure. Specifically, a single DPD inactivator or a combination of two or more DPD inactivators can be admixed with a single patient sample. Generally, the one or more DPD inactivators can be used at a total amount to reach a final concentration in the admixture sufficient to substantially inhibit the activity DPD in the patient sample (e.g., urine, whole blood, serum or plasma) and to prevent any significant or meaningful 5-FU degradation in the sample, under normal conditions of sample handling and storage and for a sufficient time to allow assays for 5-FU to be completed. For example, the total final concentration of any DPD inactivator(s) in the patient sample can range from about 1 ng/ml to about 60 µg/ml or more. For another example, one or more DPD inactivators are added and admixed in a patient sample at an amount sufficient to inhibit DPD activity in a patient sample such that there is no more than 10% degradation of 5-FU in the patient sample within about 0.5 hour after the sample is obtained from the patient and placed under room temperature (about 25° C.), preferably no more than 10% degradation of 5-FU in the patient sample within about 10 hours after the sample is obtained and placed under room temperature. As will be apparent to a skilled artisan, the amount of DPD inactivator used can vary depending on the inhibition activity of a particular DPD inactivator and the amount of DPD in a particular sample. Skilled artisans can readily determine an optimal amount of any particular DPD inactivator by routine experimentation, as demonstrated in the examples below.

The samples processed by the method of the present invention are particularly suitable for use in assays for 5-FU level, as 5-FU degradation in the samples after they are drawn but before assaying is minimized. Accordingly, the present invention further provides a method for assaying 5-FU in a patient sample from a patient administered 5-FU or a prodrug thereof. The method generally includes at least the steps of providing a processed patient sample obtained from a patient administered 5-FU or a prodrug thereof, as described above, wherein the sample is admixed in vitro with an inactivator of the enzyme dihydropyrimide dehydrogenase (DPD), and measuring the amount of 5-FU in the sample. In some embodiments, the amount of 5-FU in the sample is measured in the presence of the DPD inactivator.

In one embodiment, the method of assaying 5-FU comprises obtaining a blood sample containing 5-fluorouracil from a patient administered 5-FU, admixing the blood sample with a DPD inactivator to form a mixture, and measuring the amount of 5-FU in the mixture.

In another embodiment, the method of assaying 5-FU comprises obtaining a blood sample containing 5-FU from a patient treated with 5-FU, admixing the blood sample with a DPD inactivator to form a mixture, isolating plasma containing 5-FU and the inactivator from the mixture, and measuring the amount of 5-FU in the plasma. In preferred embodiments, the step of isolating plasma from the blood sample admixed with a DPD inactivator is performed within 4 or 5 hours, more preferably within 1 hour, from the time the blood is drawn.

In another embodiment, the method of assaying 5-FU comprises obtaining a blood sample containing 5-FU from a patient treated with 5-FU, isolating plasma from the blood sample, admixing the separated plasma with a DPD inactivator to form a mixture, and measuring the amount of 5-FU in the mixture.

Any 5-FU assay techniques known in the art may be used in measuring 5-FU levels in the samples obtained by the method of present invention. For example, methods for quantitatively assaying 5-FU by HPLC are generally known in the art. Gas liquid chromatography (GLC) and GC-MS are commonly used for measuring 5-FU concentration. Liquid chromatography tandem mass spectroscopy (LC-MSMS) is increasingly popular for 5-FU quantification. Alternatively, U.S. Pat. No. 7,205,116, which is incorporated herein by reference, discloses 5-FU immunoassays for quantification of 5-FU in plasma samples using antibodies specifically immunoreactive with 5-FU.

Thus, in one embodiment, the method of assaying 5-FU of the present invention includes measuring 5-FU in a patient sample containing 5-FU obtained from a patient administered 5-FU or a prodrug thereof using an immunoassay, wherein the patient sample is admixed in vitro with a DPD inactivator after being obtained from the patient. That is, the measuring step comprises contacting the patient sample containing 5-FU with an antibody immunoreactive with 5-FU and determining the binding of 5-FU to the antibody. 5-FU antibody is known in the art and is disclosed in, e.g., U.S. Pat. No. 7,205,116. The patient sample can be blood, serum, plasma, urine, etc., and preferably a plasma sample prepared by the sample processing methods described above. Preferably, the step of determining the binding of 5-FU to a 5-FU antibody is performed in the presence of a DPD inactivator as described above, e.g., 5-iodouracil, 5-vinyluracil, eniluracil or gimeracil.

In the following illustrative examples, 5-FU was measured using an antibody-based agglutination assay on the Olympus AU680 Analyzer using an antibody disclosed in U.S. Pat. No. 7,205,116. Specifically, two separate reagents are provided: a first reagent comprises a plurality of 5-FU molecules conjugated to a polymer or substrate, and a second reagent comprises a plurality of 5-FU antibodies attached to a solid support (e.g., a nanoparticle or bead). When the two reagents are mixed in the absence of free 5-FU, they will form large aggregates of nanoparticles and scatter light to result in a higher absorption value. In the presence of free 5-FU, e.g., when mixed with a patient sample containing 5-FU, the agglutination reaction becomes somewhat inhibited and the scattering of light is to a less extent, causing a lower absorption value. Thus, the concentration of 5-FU in a sample is measured based on the absorbance of a sample, which is determined by the amount of aggregation by first and second reagents. The instrument is calibrated with a plurality of reference samples with different known concentrations of 5-FU, and a standard curve is generated (Absorbance vs. 5-FU concentration). Absorbance values from individual samples are compared against this curve to determine concentration.

Thus, in a specific embodiment, the step of measuring 5-FU in the assaying method of the present invention comprises contacting a first reagent having a plurality of 5-FU molecules conjugated to a polymer or substrate, and a second reagent having a plurality of 5-FU antibodies attached to a solid support, in the presence of a patient sample containing 5-FU, and determining the aggregation of first and second reagents. The patient sample can be blood, serum, plasma, urine, etc., and preferably a plasma sample prepared by the sample processing methods described above. Preferably, the step of determining the binding of 5-FU to a 5-FU antibody is performed in the presence of a DPD inactivator as described above, e.g., 5-iodouracil, 5-vinyluracil, eniluracil or gimeracil.

Accordingly, in another aspect, the present invention also provides a composition comprising (1) an antibody selectively immunoreactive with 5-FU and (2) a DPD inactivator. In one embodiment, the composition comprises a patient sample (blood, serum, plasma, urine, etc.) containing 5-FU and obtained from a patient treated with 5-FU or a prodrug thereof, in admixture with (1) an antibody selectively immunoreactive with 5-FU and (2) a DPD inactivator. Preferably the antibody is not substantially immunoreactive with the DPD inactivator, and at an amount in the composition sufficient to bind substantially all 5-FU molecules in the composition. Preferably, the antibody in the composition has less than 25%, preferably less than 15%, cross-reactivity with the DPD inactivator. Examples of the antibody include those disclosed in U.S. Pat. No. 7,205,116. Suitable DPD inactivators are as described above, including, but not limited to, e.g., gimeracil, 5-iodouracil, 5-vinyluracil, and eniluracil. The amount of such DPD inactivators to be included in the composition is also as described above. Preferably, a DPD inactivator is included in the composition at an amount of at least 600 ng/ml or at least 850 ng/ml.

In one embodiment, the composition comprises (1) a plurality of antibodies attached to a solid support and selectively immunoreactive with 5-FU; (2) a plurality of 5-FU molecules conjugated to a polymer or substrate; and (3) a DPD inactivator. Preferably, the antibodies in the composition have less than 25%, preferably less than 15%, cross-reactivity with the DPD inactivator. Optionally, the composition further includes a patient sample (blood, serum, plasma, urine, etc.) containing 5-FU and obtained from a patient treated with 5-FU or a prodrug thereof.

The present invention also provides a composition comprising a sample isolated from a patient administered 5-FU or a prodrug thereof, in admixture with a DPD inactivator. Preferably the DPD inactivator is gimeracil. Also preferably the sample is blood or plasma or serum, and the inactivator is at a concentration of at least 600, 850, 1000, 1200, 2000 or 4000 ng/ml in the composition.

In another aspect, the present invention provides a kit having in a container: a sample (blood, plasma or serum) isolated from a patient administered 5-FU or a prodrug thereof, in admixture with an inactivator of DPD at a concentration of at least 600 ng/ml, 850 ng/ml, 1000 ng/ml, 1200 ng/ml, 2000 ng/ml or 4000 ng/ml. Optionally, the kit further includes means for cooling the sample to a temperature below 10° C. For cooling the sample in a container such as a Styrofoam box or a FedEx envelop, cooling packs such as PolarPack® (Tegrant) and ThermoSafe® can be used. Regular ice, or dry ice can also be used.

An assay kit is also provided, comprising in a compartmentalized container, (1) a plurality of antibodies attached to a solid support and selectively immunoreactive with 5-FU; (2) a plurality of 5-FU molecules conjugated to a polymer or substrate; and (3) a DPD inactivator. Preferably, the antibodies in the kit have less than 25%, preferably less than 15%, cross-reactivity with the DPD inactivator. The kit optionally also contains in a separate compartment 5-FU for use as a reference material. The kit would make it possible for a convenient and easy to use method of determining 5-FU level in any given patient sample.

In the various aspects of the present invention, preferably the patient sample in admixture with a DPD inactivator is not frozen within 1 hour, 2 hours, 3 hours, 4 hours, or within 5 to 48 hours after separation from a patient.

The method of assaying 5-FU is particularly useful in optimizing treatment with 5-FU or a prodrug of 5-FU wherein blood 5-FU level is determined after one dose of the drug and used as a reference to adjust/determine the follow-on dose of the drug. Thus, in yet another aspect of the present invention, a method of treating a patient with 5-FU or a 5-FU prodrug is also provided. Generally, the method comprises the steps of (1) administering to a patient in need of treatment a first dose of 5-FU or a 5-FU prodrug; (2) determining the amount of 5-FU in a sample obtained from the patient, wherein the sample is admixed in vitro with an inactivator of dihydropyrimide dehydrogenase; and (3) administering to the patient a second dose of 5-FU or a prodrug thereof. The amount of 5-FU or the prodrug administered in the second dose can be determined based on the measured 5-FU level in the patient sample in reference to a predetermined optimal or target 5-FU AUC. The second dose can then be administered in an amount to provide a blood 5-FU concentration within the target concentration. In this treatment method, the step of determining the amount of 5-FU in a sample obtained from the patient may comprise assaying 5-FU in a patient sample according to the assaying method of the present invention as described above, which incorporates the sample processing method of the present invention also described above. However, a physician may also order such an assay from a diagnostic lab and determining a 5-FU level from the assay report sent back from the lab.

For example, in therapies involving 5-FU, the quantitative target blood concentration of 5-FU, as expressed by Area Under the Curve (AUC), has been proposed to be from 20 to 24 mg·h/L. In one embodiment, the treatment method of the present invention is used to optimize 5-FU dosing, and comprises the steps of: (1) administering to a patient a first dose of 5-FU, which can be at an amount determined by, e.g., BSA (body surface area), (2) determining the amount of 5-FU in a sample obtained from the patient, wherein the sample is admixed in vitro with an inactivator of DPD, and (3) based on the amount of 5-FU measured in step (2), administering to the patient a second dose of 5-FU in an amount calculated or expected to provide a blood/plasma 5-FU AUC within the range of 20 to 25 mg·h/L. That is, if the measured 5-FU level in the patient sample indicates a blood/plasma 5-FU AUC below 20 mg·h/L, then it is recommended that the physician increases the amount of 5-FU administered in the second dose over the amount in the first dose. If the measured 5-FU level in the patient sample indicates a blood/plasma 5-FU AUC above 25 mg·h/L, then it is recommended that the physician reduces the amount of 5-FU administered in the second dose as compared to the amount in the first dose. For assaying 5-FU, the assaying method and various embodiments thereof have been described above and are incorporated herein without repeating. In a preferred embodiment, the determining step of the treatment method comprises obtaining a blood sample containing 5-FU from a patient treated with 5-FU, admixing the blood sample in vitro with a DPD inactivator to form a mixture, isolating plasma containing 5-FU and the inactivator from the mixture, and measuring the amount of 5-FU in the plasma.

Alternatively stated, the present invention provides the use of an inactivator of DPD for manufacturing an assay kit for measuring 5-FU in a patient sample for guiding the treatment of the patient with 5-FU or a prodrug thereof, wherein the treatment comprises the steps of (1) administering to a patient in need of treatment a first dose of 5-FU or a 5-FU prodrug; (2) determining the amount of 5-FU in a sample obtained from the patient, wherein the sample is admixed in vitro with an inactivator of DPD; and (3) administering to the patient a second dose of 5-FU or a prodrug thereof, in an amount determined based on the amount of 5-FU determined in step (2), and calculated or expected to result in a blood/plasma 5-FU AUC within a predetermined reference range, e.g., the range of 20 to 25 mg·h/L. The components of the assay kit are as described above or those below.

II. Devices and Kits

Figure 6:
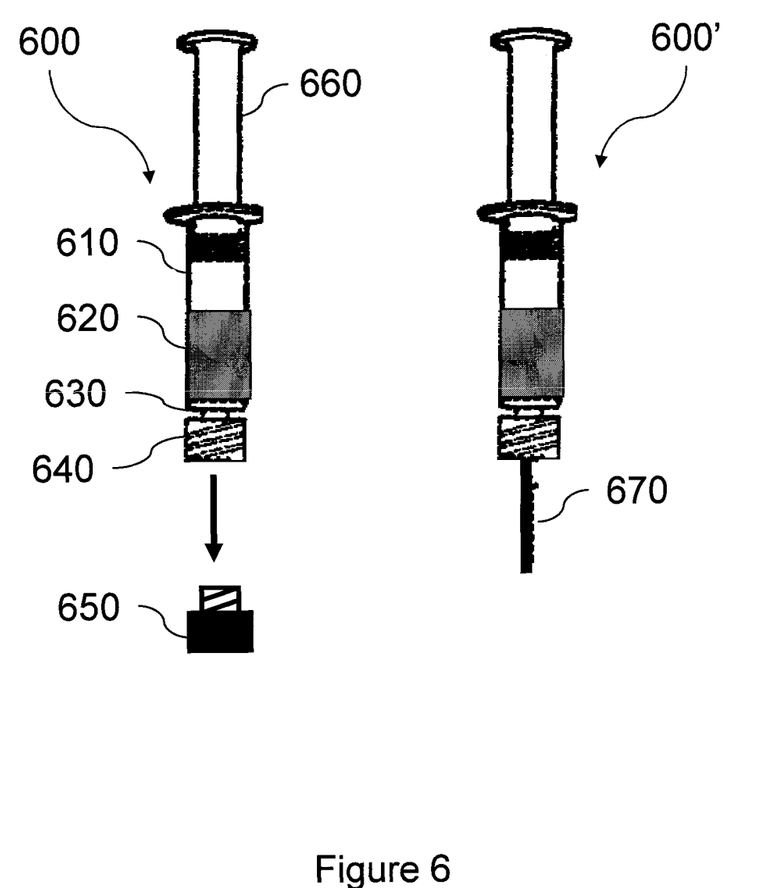
FIG. 6 is a drawing showing an embodiment of a transferring syringe assembly.

The present invention also provides transferring devices for transferring a DPD inactivator to, and admixing the DPD inactivator with, a patient blood sample. It is noted the present invention encompasses the transferring syringe assemblies described below with or without a DPD inactivator therein. Referring to FIG. 6, transferring syringe assemblies 600 and 600' are particularly useful in storing and shipping a DPD inactivator solution to a clinic or testing lab, and transferring the stored DPD inactivator solution to a patient sample. Transferring syringe assembly 600 (600 and 600') includes a barrel 610 defining a chamber of the transferring syringe, which may be prefilled with a DPD inactivator solution 620 (e.g., a solution of gimeracil or eniuracil in a DMSO or methanol solvent). Barrel 610 has a tip 630 extending from a distal end. The tip 630 can be operably connected to a needle at the time of use. In addition, transferring syringe assembly further includes a tip shield 640 attached to the tip or extending from the distal end of barrel 610. Tip shield 640 extends longitudely over tip 630. Further, the transferring syringe assembly 600 includes a tip cap 650 that can be operably connected to tip 630 or tip shield 640. In preferred embodiments, tip shield 640 and tip cap 650 have mating grooves and are interlocked together. For example, tip shield 640 can have an inward groove and tip cap 650 has an outward groove, or vise versa, such that tip cap 650 is tightly screwed upon and interlocked with tip shield 640 so as to seal the tip 630 of the barrel chamber. A plunger 660 is slidably inserted inside the chamber of barrel 610.

Transferring syringe assembly 600' is the same as transferring syringe assembly 600 except a needle 670 is attached to the syringe tip 630. The needle is preferably shielded with a needle cap. The needle can be used to puncture another container (vial or tube) containing a patient sample to deliver the DPD inactivator solution into the patient sample container by sliding or pushing plunger 660.

Figure 7A:
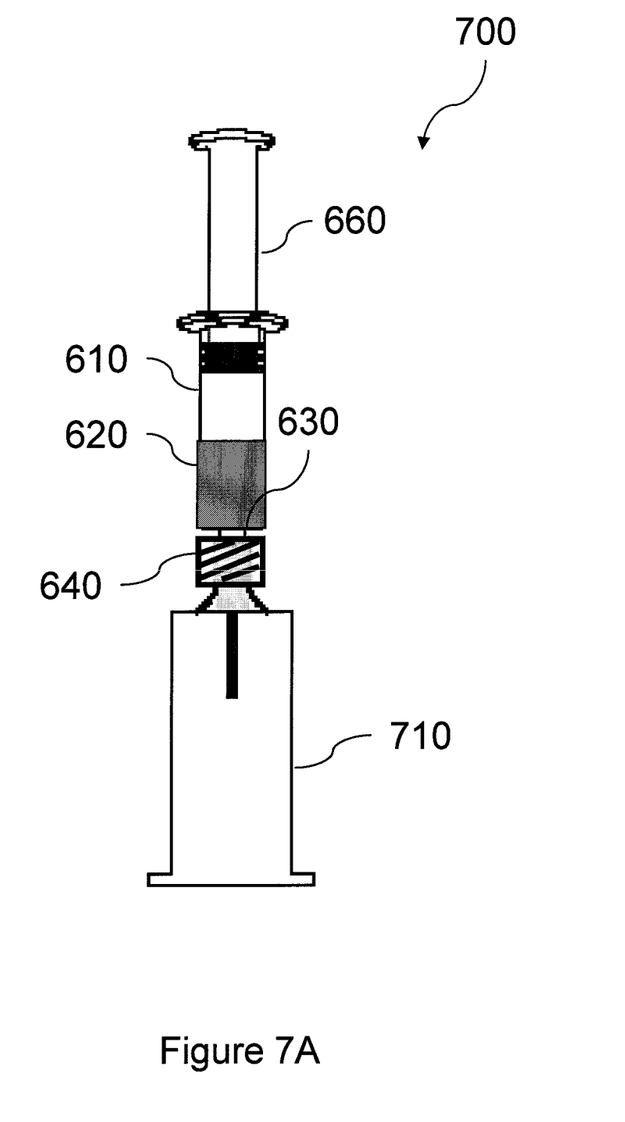
FIGS. 7A and 7B are drawings showing an embodiment of a transferring syringe assembly.
Figure 7B:
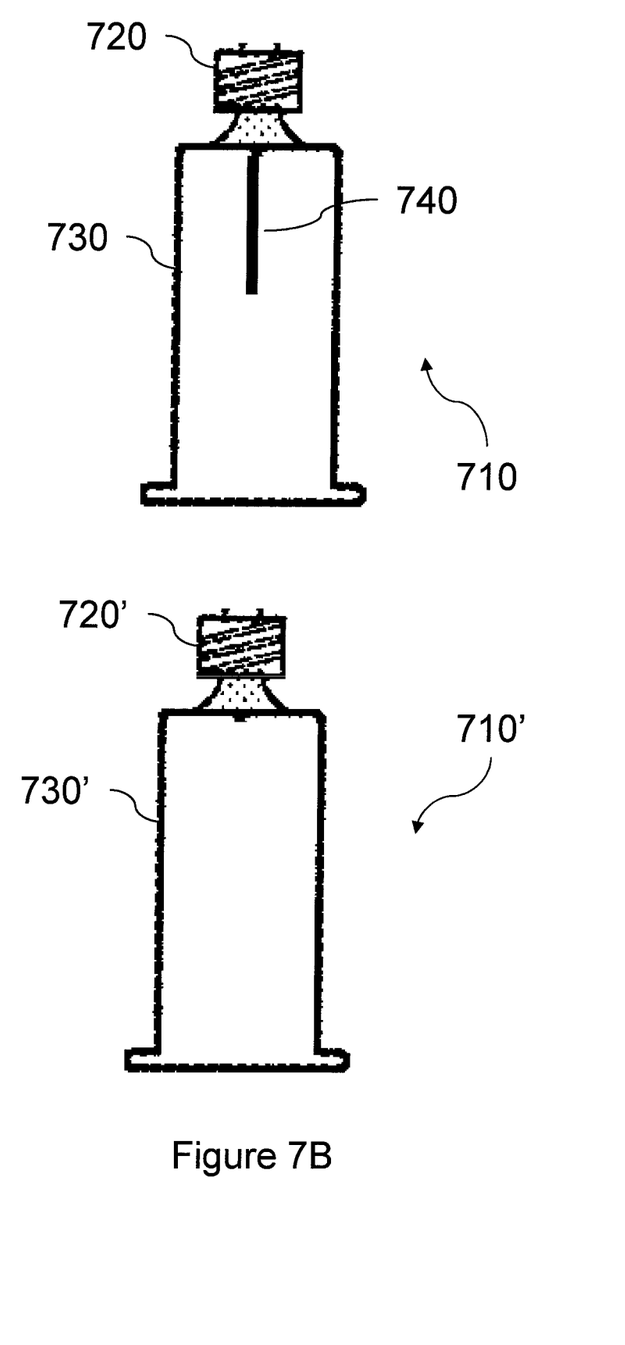

FIG. 7 illustrates another transferring syringe assembly 700, which is same as transferring syringe assembly 600 and 600' except that the tip cap 650 of the transferring syringe assembly 600 is replaced with needle cover 710, or that a needle cover 710' is mounted onto transferring syringe assembly 600'. Referring to needle cover 710, it includes a generally tubular body 730 coaxially disposed about the needle 740, and having a tubular wall extending along needle 740 and beyond the sharpened tip of the needle. The needle cover 710' is same as needle cover 710 except for the lack of the needle 740. The needle covers can be operably connected and mounted onto the transferring syringe assembly 600 or 600' forming the transferring syringe assembly 700. For example, in one embodiment, tip shield 640 of transferring syringe assembly 600 can have an inward groove for interlocking the luer adaptor 720 of needle 740. In another embodiment, tip shield 640 of transferring syringe assembly 600' can have an inward groove for interlocking the luer adaptor 720' such that needle cover 710' is mounted onto transferring syringe assembly 600' shielding needle 670. Alternatively, 720 or 720' can be a connector coaxially mounted about the needle 740.

Figure 8:
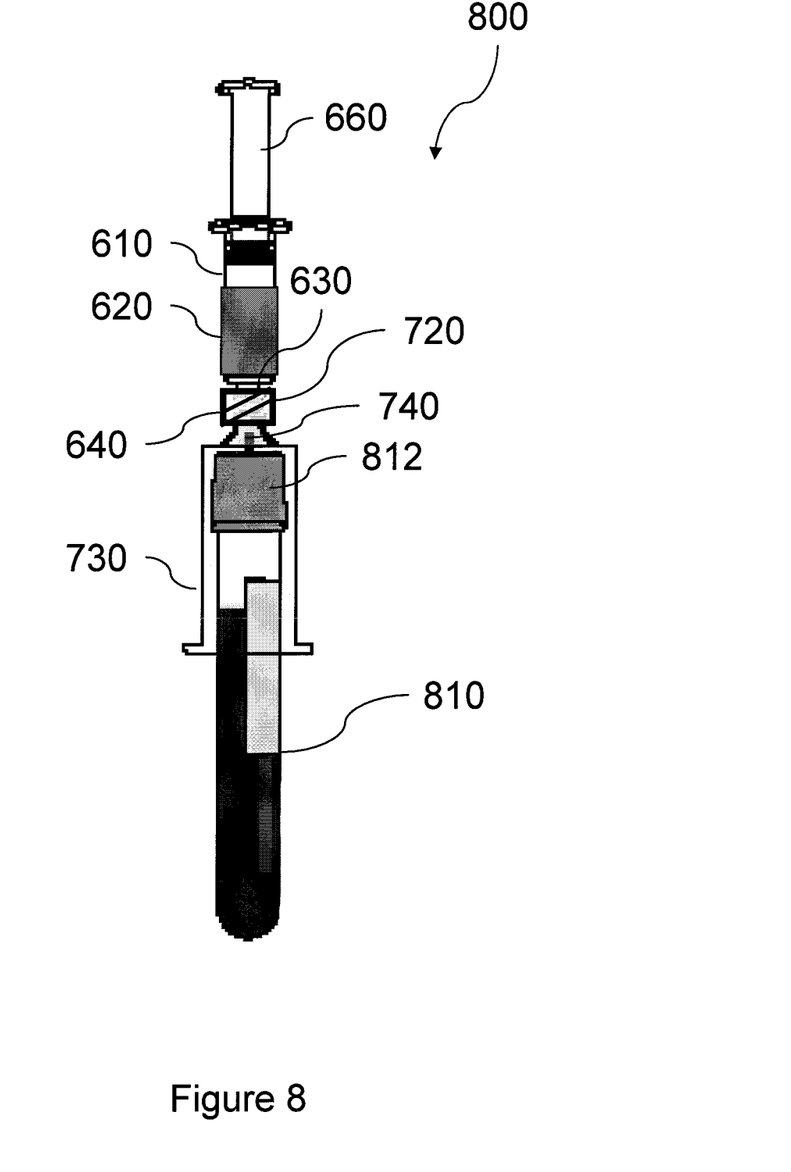
FIG. 8 is a drawing showing an embodiment of a transferring syringe assembly.

The transferring syringe assembly 700 can be used to conveniently and safely transfer a DPD inactivator solution into a patient sample tube as shown in FIG. 8. The transferring syringe assembly 800 in FIG. 8 includes the transferring syringe assembly 700 and a tube 810 containing a patient sample (e.g., blood) wherein the tube 810 is inserted into the needle cover 710 or 710' and needle 740 or 670 has been inserted into the sample tube 810 through the puncturable cap 812 of the tube. In this manner, the plunger 660 can be pushed thereby delivering the DPD inactivator solution into the sample tube, if the DPD inactivator solution is contained in the transferring syringe assembly 700.

In yet another aspect, the present invention provides a kit including, one or more the transferring syringe assemblies described above. The kit may or may not include a DPD inactivator in any form (e.g., in solution). If included, the DPD inactivator can be stored in a transferring syringe assembly, or in a separate compartment, and can be at an amount sufficient to inhibit DPD enzymatic activity in a patient blood sample and to prevent 5-FU degradation in the sample. The kit may further include one or more of the following items: disposable pipettes, blood drawing tubes, cryovial tubes for receiving and storing plasma samples, transportation tubes, bags with absorbent materials for transporting a patient sample, etc. The kit may further include instruction sheets explaining to healthcare professionals how to obtain and process patient samples for the purposes of assaying 5-FU in the samples, which are all described in detail above. In addition, the kit may include an antibody selectively immunoreactive with 5-FU. This kit optionally also contains in a separate compartment 5-FU for use as a reference material.

In one embodiment, the kit comprises in a container, (1) a transferring syringe assembly as illustrated in FIG. 6 or FIG. 7, (2) a DPD inactivator, and (3) an antibody selectively immunoreactive with 5-FU. In another embodiment, the kit comprises in a container, (1) a transferring syringe assembly illustrated in FIG. 6 or FIG. 7, (2) a DPD inactivator, (3) a plurality of antibodies attached to a solid support and selectively immunoreactive with 5-FU; (4) a plurality of 5-FU molecules conjugated to a polymer or substrate. Preferably, the antibodies in the kit have less than 25%, preferably less than 15%, cross-reactivity with the DPD inactivator. The kit optionally also contains in a separate compartment 5-FU for use as a reference material. Also preferably, the DPD inactivator is in a solution contained in the barrel of the transferring syringe assembly.

In the following illustrative examples, 5-FU was measured using an antibody-based agglutination assay on the Olympus AU680 Analyzer using an antibody disclosed in U.S. Pat. No. 7,205,116. Specifically, the concentration of 5-FU in a sample is determined based on the absorbance of a sample, which is determined by the amount of aggregation by the nanoparticles. The system requires two reagents, which when mixed in the absence of free 5-FU will form large aggregates of nanoparticles and scatter light to result in a higher absorption value. In the presence of free 5-FU, the agglutination reaction becomes somewhat inhibited and scattering of light is less, causing a lower absorption value. The instrument is calibrated twice monthly, and a curve is generated (Absorbance vs. 5-FU concentration). Absorbance values from individual samples are compared against this curve to determine concentration.

Generally in the agglutination assay, 95 µl of a buffer containing 5-FU-labeled amino-dextran is pipetted to a cuvette, followed by 7 µL of a filtered plasma sample. The sample and reagent are mixed and then incubated for about 3.5 minutes. 95 µl of 5-FU antibody-conjugated nanoparticles is pipetted into the cuvette and mixed. The complete reaction incubates for about 6.2 minutes. A series of 27 measurements at 600 nm are taken at regular intervals by the AU680 analyzer throughout this process, and 5-FU concentration is calculated using the measurements from two specific time points.

III. Examples

1. Use of Eniluracil as Stabilizer

Six tubes of blood (spray-on $K_2$EDTA tubes, 6 mL) was drawn from each of six donors, and blood tubes were gently inverted several times to mix anti-coagulant. Blood was pooled and kept separate by donor. An aliquot of each blood sample was transferred to a new conical tube, and a calculated volume of stock 5-FU (at 200 ng/µL) was spiked into each blood sample for a final concentration of 500 ng/mL 5-FU. Each blood sample was aliquotted to a set of six tubes (5 mL of blood per tube) containing eniluracil under the following conditions:

High concentration (4000 ng/mL final in blood), DMSO solvent;

Low concentration (1000 ng/mL final in blood), DMSO solvent.

Figure 2:
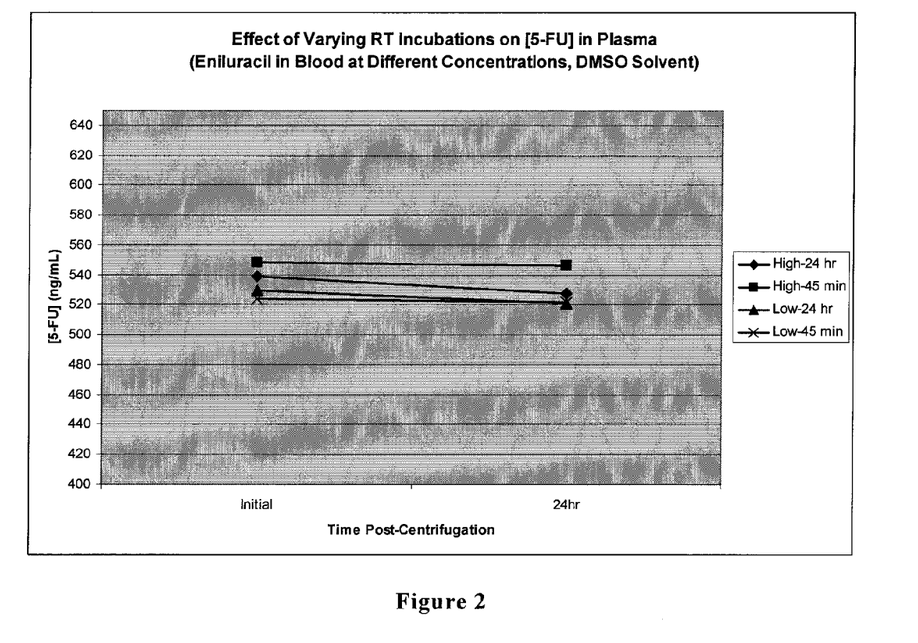
FIG. 2 is a graph showing that eniluracil was effective in an preventing degradation of 5-FU in blood samples.

In addition, blood was added to tubes containing only DMSO (no eniluracil) to serve as negative controls. All blood tubes were mixed by inversion. The blood tubes were incubated at room temperature for 45 minutes or 24 hours, and at the appropriate time, tubes were centrifuged at 2000×g for 10 minutes at room temperature to separate plasma. Plasma was aspirated immediately following centrifugation, and dispensed into clean cryovials. Samples were run under standard conditions for Olympus analyzer AU680 (200 µL, spin for 15 minutes at 12,500 rpm). Measurements were taken immediately after plasma collection and 24 hours after the initial reading. Plasma was stored at room temperature. FIG. 2 shows that eniluracil was effective in preventing degradation of 5-FU in blood samples.

2. Use of 5-Vinyluracil, 5-Iodouracil, and Gimeracil as Stabilizer

Three tubes of blood (spray-on $K_2$EDTA tubes, 10 mL) was drawn from each of six donors, and blood tubes were gently inverted several times to mix anti-coagulant. Blood was pooled and kept separate by donor. An aliquot of each blood sample was transferred to a new conical tube, and a calculated volume of stock 5-FU (at 200 ng/µL) was spiked into each blood sample for a final concentration of 500 ng/mL 5-FU. Each blood sample was aliquotted to a set of four tubes (5 mL blood per tube). Each set of tubes was different, but included a combination of the conditions below:

Low concentration of 5-iodouracil (10 µg/mL final in blood);

High concentration of 5-iodouracil (40 µg/mL final in blood);

Low concentration of 5-vinyluracil (5 µg/mL final in blood);

High concentration of 5-vinyluracil (20 µg/mL final in blood);

Low concentration of gimeracil (300 ng/mL final in blood);

High concentration of gimeracil (1,200 ng/mL final in blood).

Figure 3:
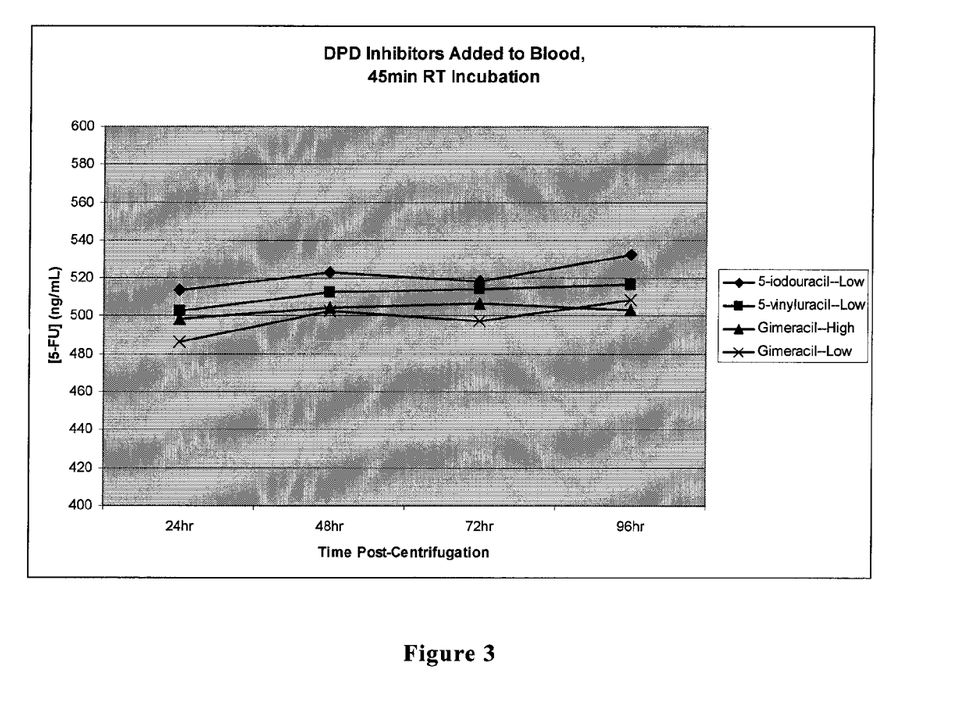
FIG. 3 is a graph showing that 5-vinyluracil, 5-iodouracil, and gimeracil were all effective in stabilizing 5-FU in blood samples.

Tubes were mixed by inversion. Blood tubes incubated at room temperature for 45 minutes. At the appropriate times, blood tubes were centrifuged at 2000×g for 10 minutes at room temperature to separate plasma. Plasma was aspirated immediately following centrifugation, and dispensed into new conical tubes. Plasma samples were run under standard conditions for Olympus AU680 analyzer (200 µL, spin for 15 minutes at 12,500 rpm). Plasma was stored at room temperature. FIG. 3 shows that 5-vinyluracil, 5-iodouracil, and gimeracil were all effective in stabilizing 5-FU in blood samples.

3. The Amount of DPD Inactivator Needed

Four tubes of blood (spray-on $K_2$EDTA tubes, 10 mL) was drawn from each of six donors, and gently inverted several times to mix anti-coagulant. All donor blood was pooled into one large tube, and two equal aliquots of that pooled blood were transferred to two new tubes. The remaining blood was used to isolate white blood cell (WBC)/buffy coat. WBC/buffy coat was isolated by centrifuging the remaining blood tubes, extracting and pooling the WBC layer from each tube, centrifuging again to enrich the WBC/buffy coat, and separating the enriched WBC/buffy coat layer into a clean tube. One volume of blood was spiked with a calculated volume of stock 5-FU (at 200 ng/μL) for a final concentration of 500 ng/mL, and the other volume of blood was spiked with a calculated volume of stock 5-FU (at 200 ng/μL) for a final concentration of 1500 ng/mL. Three sets of eight tubes each were prepared to aliquot the spiked blood into. In addition, a negative control was used that was inoculated with 300 μL of 30% methanol/water instead of gimeracil. To four of the eight tubes per set, the low concentration 5-FU blood was aliquotted, 6 mL each tube. The high concentration 5-FU blood was aliquotted to the remaining four tubes per set, as well as to the negative control tube, 6 mL each. The eight tubes were then inoculated with either 300 μL of 0.12 mg/mL gimeracil in 30% MeOH/water or 300 μL of 0.04 mg/mL gimeracil. Blood tubes were inverted to mix the gimeracil, and then sat at room temperature for 45 minutes. Blood tubes were centrifuged at 2000×g for 10 minutes and room temperature. Plasma was aspirated immediately after centrifugation and dispensed into clean cryovials. The WBC/buffy coat was added to designated tubes of plasma, and vortexed to evenly mix. Plasma samples were run under standard conditions for the AU680 analyzer (200 μL, spin for 15 minutes at 12,500 rpm). Measurements were taken immediately after adding WBC/buffy coat ("initial"), as well as 24 hours ("24-hour"), after addition of WBC/buffy coat. For the 24-hour measurement, plasma was stored at room temperature for the first 24 hours of the experiment to simulate overnight ambient shipping. Table 1 below summarizes the results.

TABLE 1

| Target 5-FU Concentration | Gimeracil concentration (ng/mL) | WBC | Average 5-FU Measurement | | % change (Initial vs. 24-hour) |
|---|---|---|---|---|---|
| | | | Initial | 24-hour | |
| 500 ng/mL | 2000 | w/WBC | 465.8 | 478.6 | 2.7% |
| | 2000 | NO WBC | 488.3 | 474.3 | −2.9% |
| | 6000 | w/WBC | 473.7 | 478.6 | 1.0% |
| | 6000 | NO WBC | 479.1 | 487.3 | 1.7% |
| 1500 ng/mL | 2000 | w/WBC | 1377.7 | 1418.1 | 2.9% |
| | 2000 | NO WBC | 1434.9 | 1427.3 | −0.5% |
| | 6000 | w/WBC | 1402.9 | 1390.1 | −0.9% |
| | 6000 | NO WBC | 1430.3 | 1458.3 | 2.0% |
| | 0 | w/WBC | 1267.4 | 856 | −32.5% |

Figure 4:
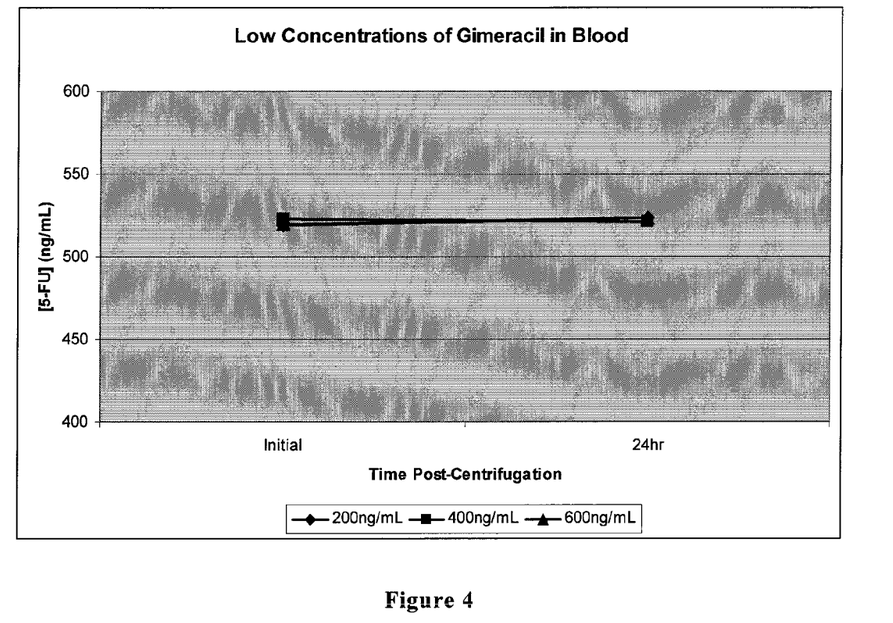
FIG. 4 is a graph showing that low concentrations of gimeracil in blood is effective in inhibiting DPD-mediated degradation of 5-FU.

Four tubes of blood (spray-on $K_2$EDTA tubes, 10 mL) was drawn from each of five donors, and gently inverted several times to mix anti-coagulant. Blood was pooled by donor into conical tubes. An aliquot of each donor's blood was transferred to a clean tube. A calculated volume of 5-FU stock (at 200 ng/μL) was added to each blood sample to achieve a final concentration of 500 ng/mL 5-FU, and tubes were inverted to mix. Spiked blood was aliquotted into clean tubes, nine tubes per donor and 3.5 mL of blood per tube. Gimeracil was added to the tubes at a final concentration of 200, 400, or 600 ng/mL for each tube. In addition, in control samples, methanol was added to the blood instead of gimeracil, in order to serve as a negative control. The blood tubes sat at room temperature for 45 minutes after the addition of the gimeracil or methanol. At the appropriate times, the blood tubes were centrifuged at 2000×g for 10 minutes at room temperature to separate plasma. Plasma was aspirated immediately after centrifugation, and the plasma was dispensed into clean tubes. Plasma samples were run using standard conditions for Olympus AU680 analyzer (200 μL, spin for 15 minutes at 12,500 rpm). Measurements of 5-FU concentration were taken after plasma collection ("initial") and 24 hours ("24 hr") thereafter. For the 24 hr measurement, plasma was stored at room temperature during the 24 hours. Table 2 summarizes the results. As shown in Table 2 and FIG. 4, low concentrations of gimeracil in blood is also effective at inhibiting DPD-mediated degradation of 5-FU. The overall percent difference in 5-FU concentration between the samples containing 200 ng/mL and 600 ng/mL gimeracil is less than 1%.

TABLE 2

| Concentration of Gimeracil | Initial | 24 hr |
|---|---|---|
| 200 ng/mL | 518.7 | 523.4 |
| 400 ng/mL | 523.0 | 521.6 |
| 600 ng/mL | 519.5 | 523.3 |

4. Effect of Extended Incubation of Gimeracil in Blood Before Plasma Separation

Six tubes of blood (spray-on $K_2$EDTA tubes, 6 mL) was drawn from each of six donors, and the blood tubes were inverted several times to mix the anti-coagulant into the blood. Blood tubes were pooled and kept separate by donor. An aliquot of each donor's blood was transferred to a new tube, and a calculated volume of 5-FU stock (at 200 ng/μL) was added to each blood sample to achieve a final concentration of 500 ng/mL 5-FU. Spiked blood samples were aliquotted to clean tubes, 4 mL of blood to each of 8 tubes per donor. Gimeracil in methanol solvent was added to the blood tubes to reach a final concentration of 1200 ng/mL. For negative control, methanol only is added to the control blood tube. Blood tubes sat at room temperature for 45 minutes, 24 hours, or 48 hours before plasma separation. At the appropriate times, the blood tubes were centrifuged at 2000×g for 10 minutes at room temperature for plasma separation. The plasma was aspirated immediately after centrifugation and dispensed into clean cryovials. For 5-FU assays, the plasma samples were run under standard conditions for the Olympus AU680 analyzer, as described above (200 μL, spin for 15 minutes at 12,500 rpm). Measurements of 5-FU concentration were taken after plasma collection and for 2 days following the initial reading. Plasma was stored at room temperature during the interval. The results of this experiment are summarized in Table 3 below, and FIG. 5.

TABLE 3

| Time of incubation in blood | 5-FU Concentration (ng/ml) | |
|---|---|---|
| | Upon plasma separation | 24 hrs after plasma separation |
| 45 minute | 533.3 | 538.1 |
| 24 hours | 551.8 | 551.9 |
| 48 hours | 581.3 | 578.4 |

Figure 5:
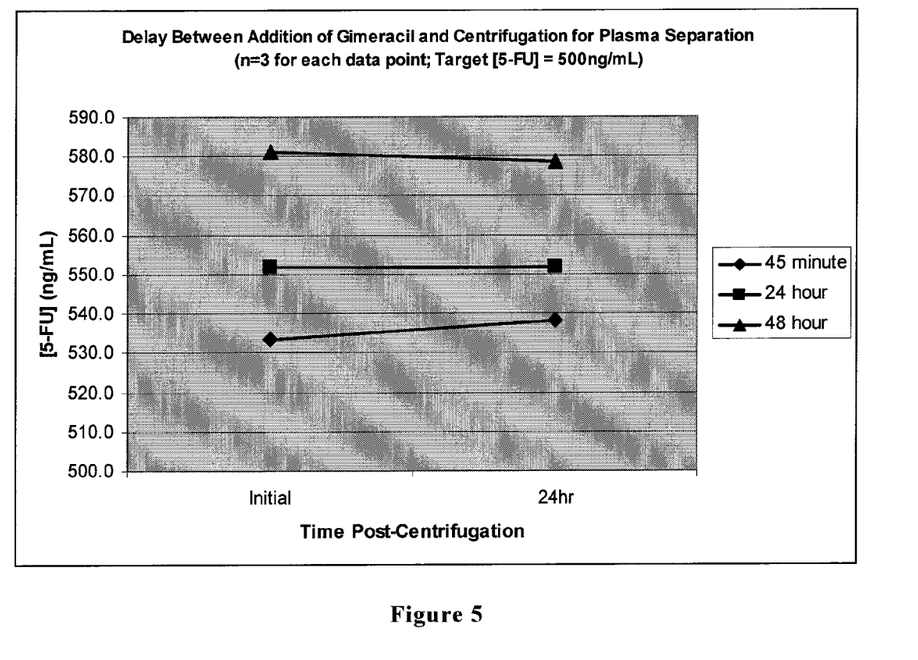
FIG. 5 is a graph showing the effect of keeping gimeracil in blood without plasma separation for a longer time.

As can be seen in FIG. 5, keeping gimeracil in blood without plasma separation for a longer time may cause 5-FU concentration to artificially increase. The blood sample preferably is centrifuged within the same day as the gimeracil inhibitor is added.

5. Assaying 5-FU in Patient Samples

Sample collection consists of venous blood drawn at the clinician site between at least 2 hours after initiation of 5-FU treatment and before the end of drug infusion to ensure steady state levels (the average $t_{1/2}$ for 5-FU is ~13 minutes). The OnDose Sample Stabilizer is injected and mixed into the blood sample immediately following the blood draw, and the blood sample can then remain at RT for up to 4 hours. The sample is then centrifuged (1500-2000 g, for 10 min). Approximately half of the plasma is transferred to a plasma transport tube, labeled with a barcode, and shipped overnight at ambient temperature to Myriad Genetic Laboratories, Inc. for analysis.

Upon receipt, the sample bar code is scanned and tracked. The samples are centrifuged through a filter membrane with the resultant filtrate used for analysis. The OnDose assay is a competitive homogenous two-reagent nanoparticle agglutination immunoassay. The first reagent contains 5-FU conjugate with the second reagent consisting of 5-FU-directed, antibody-conjugated nanoparticles. The amount of free 5-FU in the plasma inhibits the aggregation of the two assay reagents. The amount of light absorbance at certain wavelengths from nanoparticle agglutination depends on the amount of drug in the plasma. This absorbance is compared to a standardized calibration curve for quantitation. The quantitative target range, as expressed by Area Under the Curve (AUC), based on Gamelin E, et al, *J Clin Oncol.* 26(13):2099-105 (2008), is calculated from the measured concentration of 5-FU and the infusion duration provided by the clinician on the test request form.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A method of assaying 5-fluorouracil in a whole blood sample from a patient administered 5-fluorouracil or a prodrug thereof, said method comprising: measuring 5-fluorouracil in a sample obtained from said patient, wherein said sample is admixed in vitro with an inactivator of dihydropyrimidine dehydrogenase after being obtained from said patient at an amount sufficient to inhibit dihydropyrimidine dehydrogenase activity in said sample such that there is no more than 10% degradation of 5-fluorouracil in said sample within about 0.5 hour after said sample is obtained from said patient.

2. The method of claim 1, wherein said inactivator is at a concentration of at least 600 ng/ml in said sample.

3. The method of claim 1, wherein said inactivator is a pyrimidine or pyridine derivative.

4. The method of claim 3, wherein said inactivator is chosen from (a) a uracil derivative with the 5-position substituted by a moiety chosen from halogen atom, a $C_{2-4}$ alkenyl group, a $C_{2-4}$ haloalkenyl, a $C_{2-6}$ alkynyl group, a $C_{2-6}$ haloalkynyl group, a cyano group, a $C_{1-4}$ alkyl group and a $C_{1-4}$ haloalkyl group; (b) a derivative of barbituric acid; (c) a derivative of 2,4-dihydroxypyridine; and (d) a derivative of 2,6-dihydroxypyridine.

5. The method of claim 4, wherein said inactivator is chosen from the group consisting of eniluracil, 5-propynyluracil, 5-cyanouracil, 5-bromoethynyluracil, 5-(1-chlorovinyl) uracil, 5-iodouracil, 5-bromovinyluracil, (E)-5-(2-bromovinyl)uracil, 5-hex-1-ynyluracil, 5-vinyluracil, 5-trifluorouracil, 5-bromouracil and 5-(2-bromo-1-chlorovinyl)uracil, gimeracil (5-chloro-2,4-dihydroxypyridine) and 3-cyano-2,6-dihydroxypyridine.

6. The method of claim 5, wherein said inactivator is gimeracil.

7. The method of claim 1, wherein said sample is admixed in vitro with said inactivator of dihydropyrimidine dehydrogenase within 1 hour after being obtained from said patient.

8. The method of claim 1, wherein said sample is admixed in vitro with an inactivator of dihydropyrimidine dehydrogenase after being obtained from said patient at an amount sufficient to inhibit dihydropyrimidine dehydrogenase activity in said sample such that there is no more than 10% degradation of 5-fluorouracil in said sample within about 10 hours after said sample is obtained from said patient.

9. A method of processing a whole blood sample from a patient treated with a regimen comprising 5-fluorouracil or a prodrug thereof, for a 5-fluorouracil assay, said method comprising:

obtaining a whole blood sample containing 5-fluorouracil from said patient; and processing said sample by:

(1) admixing said sample with a first inactivator of dihydropyrimidine dehydrogenase, and isolating therefrom plasma containing 5-fluorouracil and said inactivator forming a second first mixture; or (2) admixing said sample with a second inactivator of dihydropyrimidine dehydrogenase to form a second mixture;

wherein said sample is admixed with said first or said second inactivator of dihydropyrimidine dehydrogenase at an amount sufficient to inhibit dihydropyrimidine dehydrogenase activity in said sample such that there is no more than 10% degradation of 5-fluorouracil in said sample within about 0.5 hour after said sample is obtained from said patient.

10. The method of claim 9, wherein said processing step comprises admixing the blood sample with a second inactivator of dihydropyrimidine dehydrogenase, and isolating therefrom plasma containing 5-fluorouracil and said inactivator forming a second mixture.

11. The method of claim 9, wherein said processing step comprises admixing the blood sample with a third inactivator of dihydropyrimidine dehydrogenase to form a third mixture.

12. The method of claim 9, wherein said inactivator is gimeracil.

13. The method of claim 9, wherein said processing step is performed within 1 hour after said obtaining step.

14. The method of claim 10, wherein said isolating is performed within 1 hour after said admixing.

15. The method of claim 9, wherein said sample is admixed with said first or said second inactivator of dihydropyrimidine dehydrogenase at an amount sufficient to inhibit dihydropyrimidine dehydrogenase activity in said sample such that there is no more than 10% degradation of 5-fluorouracil in said sample within about 10 hours after said sample is obtained from said patient.

\* \* \* \* \*